(12) United States Patent
Reicher et al.

(10) Patent No.: US 11,745,083 B2
(45) Date of Patent: Sep. 5, 2023

(54) PHYSICAL BALANCE TRAINING SYSTEM USING FOOT SENSORS, REAL-TIME FEEDBACK, ARTIFICIAL INTELLIGENCE, AND OPTIONALLY OTHER BODY SENSORS

(71) Applicant: STASIS, LLC, Santa Fe, NM (US)

(72) Inventors: Murray Reicher, Rancho Santa Fe, CA (US); Ravi Patel, San Diego, CA (US); Tanish Jain, San Diego, CA (US); Saikiran Komatineni, San Diego, CA (US); Shivani Bhakta, Los Angeles, CA (US); Albert Hernandez, Winnetka, CA (US); Jordan Levy, San Diego, CA (US)

(73) Assignee: STASIS, LLC, Santa Fe, NM (US)

(*) Notice: Subject to any disclaimer, the term of this patent is extended or adjusted under 35 U.S.C. 154(b) by 83 days.

(21) Appl. No.: 17/407,615

(22) Filed: Aug. 20, 2021

(65) Prior Publication Data

US 2022/0054926 A1 Feb. 24, 2022

Related U.S. Application Data

(60) Provisional application No. 63/067,908, filed on Aug. 20, 2020.

(51) Int. Cl.
| | |
|---|---|
| *A61B 5/375* | (2021.01) |
| *A63B 71/06* | (2006.01) |
| *A63B 24/00* | (2006.01) |
| *A61B 5/00* | (2006.01) |

(52) U.S. Cl.
CPC ........ *A63B 71/0622* (2013.01); *A61B 5/4023* (2013.01); *A61B 5/486* (2013.01); *A61B 5/6807* (2013.01); *A63B 24/0062* (2013.01); *A63B 2071/0625* (2013.01); *A63B 2071/0655* (2013.01); *A63B 2071/0694* (2013.01); *A63B 2220/30* (2013.01); *A63B 2220/40* (2013.01); *A63B 2220/56* (2013.01); *A63B 2220/803* (2013.01); *A63B 2220/836* (2013.01); *A63B 2225/50* (2013.01)

(58) Field of Classification Search
CPC ............ A63B 71/0622; A63B 24/0062; A61B 5/4023; A61B 5/486; A61B 5/6807
See application file for complete search history.

(56) References Cited

U.S. PATENT DOCUMENTS

| | | | |
|---|---|---|---|
| 2017/0273599 A1* | 9/2017 | Reese | .................. A61B 5/6807 |
| 2019/0283247 A1* | 9/2019 | Chang | .................... G05B 17/02 |

\* cited by examiner

*Primary Examiner* — Robert P Bullington
(74) *Attorney, Agent, or Firm* — Jonathan Kidney; Intelink Law Group, P.C.

(57) ABSTRACT

A wearable, flexible, bio-sensing housing with physical feedback, with software running on a user's wirelessly connected smart device. The housing has embedded at least one of pressure, movement, temperature, velocity, and acceleration sensors, and at least one of a haptic, vibrational, audio, visual, kinesthetic, tactile, olfactory, thermal, vestibular, and somatosensory feedback mechanisms. The feedback being triggered by measurements from the sensors and predetermined parameters, as compared by the smart device's software and/or a connected server. With real-time measurements and real-time feedback directly to the user's body, the user can perform real-time adjustment of his activity to obtain optimal performance and/or health.

16 Claims, 8 Drawing Sheets

PHYSICAL BALANCE TRAINING SYSTEM USING FOOT SENSORS, REAL-TIME FEEDBACK, ARTIFICIAL INTELLIGENCE, AND OPTIONALLY OTHER BODY SENSORS

CROSS-REFERENCE TO RELATED APPLICATION(S)

This application claims the benefit of U.S. Provisional Patent Application No. 63/067,908, filed Aug. 20, 2020, the contents of which is hereby incorporated by reference in its entirety.

FIELD

The present invention is directed to a wearable bio-sensor with user feedback. More particularly, the invention is directed to a body-part conforming, non-intrusive, wearable (e.g., sole, sleeve, etc.) bio-sensor capable of monitoring at least pressure, acceleration, or motion while providing the user feedback relative to target performance to form a real-time "training system."

BACKGROUND

Humans seeking to improve their athletic or other physical performance or improve physical balance in daily life today practice or undergo training in various ways. They may observe experts in-person or via various media or may receive instruction in person from professionals. Learning to improve physical performance can be subdivided into tasks of observation, imitation with correction, followed by repetition with feedback. For example, a human may seek to improve a golf swing, baseball pitching, fielding, or batting performance, various basketball skills, skiing, surfing, skateboarding, gymnastics, yoga, running speed, jumping ability, dancing ability, walking skills, weightlifting, or other various acts of physical performance related to a job or recreational task. In addition, people often seek to coordinate motion between multiple people (e.g., dancing or marching in a group), master a musical instrument (such as drums), or complete various athletic, musical, or job tasks in coordination with other people. These examples of physical tasks all have in common the coordinated movement of one or more feet or body parts of one or more people.

In existing physical monitoring systems, individuals do not receive real-time feedback to improve their balance and coordination as they perform. For example, there is no existing system that provides a golfer real-time feedback related to the timing of specific foot pressure changes, acceleration, velocity, and movement, nor are there systems that provide such feedback in relation to similar measurements of other body parts. More specifically, for example, there is no monitoring system that provides real-time feedback related to measures of a golfer's arms, shoulders, hips, or head in relation to measures of his or her feet in real-time. Moreover, in the example of a golfer, there is no system that can analyze such measures in an expert golfer in order to provide a subsequent user real-time feedback to enable the user to imitate the expert, to understand deviations from the expert, and to match the user with the most appropriate expert to imitate. Therefore, existing technology does not optimally facilitate the imitation with correction or repetition with feedback phases of mastering a skill. Beyond this, no technology facilitates the coordinated movements and pressure changes among groups of individuals seeking to synchronously coordinate their actions. The present invention seeks to overcome certain of these limitations and other drawbacks of the prior art, and to provide new features not heretofore available, allowing for balance and coordinated motion training.

SUMMARY

The following presents a simplified summary in order to provide a basic understanding of some aspects of the claimed subject matter. This summary is not an extensive overview and is not intended to identify key/critical elements or to delineate the scope of the claimed subject matter. Its purpose is to present some concepts in a simplified form as a prelude to the more detailed description that is presented later.

In one aspect of the disclosed embodiments, a wearable, feedback providing bio-sensing system, comprising, a bio-sensing and feedback program running on a user's smart device, the program receiving wireless data transmitted from a proximal wearable bio-sensing device, the wearable bio-sensing device comprising, a flexible bio-sensor housing with a form factor that is body-part conforming; a controller; a powering source; a wireless communication module, wherein the controller, powering source, and wireless communication module are embedded in one or more first recesses in the housing; one or more sensors measuring at least one of pressure, movement, temperature, velocity, and acceleration, embedded in one or more second recesses in the housing, one or more sensors communicating a measurement to the controller; and one or more feedback mechanisms providing at least one of a haptic, vibrational, audio, visual, kinesthetic, tactile, olfactory, thermal, vestibular, and somatosensory feedback to a wearer of the housing, embedded in one or more third recesses in the housing, the feedback being triggered by the controller from instructions sent by the bio-sensing and feedback program, wherein the triggered feedback indicates to the user that the measured at least one pressure, movement, temperature, velocity, and acceleration conforms or does not conform to a desired parameter, enabling the user to perform real-time adjustment of his activity.

In another aspect of the disclosed embodiments, the above system is provided, wherein at least one of the one or more first, second and third recesses form a single larger recess; and/or further comprising a server, the server communicating with the smart device, and performing an analysis of data from the smart device's received sensor measurements; and/or wherein the bio-sensing and feedback program are separate programs; and/or further comprising an artificial intelligence program running on the server and analyzing the data from the smart device's received sensor measurements; and/or wherein the housing is shaped as an insole; and/or wherein the one or more sensors are disposed proximal to a ball-of-foot location on the insole and a heel location on the insole; and/or wherein the transmitted wireless data is communicated via Bluetooth® between the user's smart device and the wearable bio-sensing device; and/or wherein the housing is shaped as a sleeve, for fitment over a knee, elbow or foot; and/or wherein the smart device is a smart phone, smart watch, smart glasses, tablet computer, or smart earphones; and/or wherein the one or more sensors is formed from a pressure resistive material placed between two or more layers of a grid or strip of conductive material; and/or further comprising a pressure sensor disposed outside the housing, the pressure sensor composed of a pressure resistive material placed between two or more layers of a grid or strip of conductive material.

In yet another aspect of the disclosed embodiments, a method to provide real-time feedback to a user's physical activity is provided, comprising, running a bio-sensing and feedback program on a user's smart device; receiving wireless sensor data transmitted from a user-worn, flexible bio-sensing device that is body-part conforming with sensing electronics to sense at least one of pressure, movement, temperature, velocity, and acceleration, and feedback electronics to send physical feedback to the user; monitoring the user's activity through the sensing electronics; comparing the at least one of pressure, movement, temperature, velocity, and acceleration of the physical activity to a desired parameter via the bio-sensing and feedback program; and sending at least one of a haptic, vibrational, audio, visual, kinesthetic, tactile, olfactory, thermal, vestibular, and somatosensory feedback to the user, to indicate the user's physical activity conforms or does not conform to the desired parameter, enabling the user to perform real-time adjustment of his activity.

In yet another aspect of the disclosed embodiments, the above method is provided, further comprising: sending the receiving wireless sensor data to a server connected to the user's smart device; processing the sensor data; and sending instructions to the user's smart device to trigger a feedback in the user-worn, flexible bio-sensing device; and/or further comprising performing artificial intelligence on the sensor data; and/or wherein the user wears the bio-sensing device as a shoe insole, a sock, a knee sleeve, or elbow sleeve; and/or wherein the method provides a real-time balance learning methodology; and/or wherein at least one of weight, heart rate, blood pressure and cholesterol level biometric information on the user is obtained; and/or wherein the method is used to improve the user's performance with a sport; and/or wherein the method is used to track the user's progress with a medical or physical condition.

DETAILED DESCRIPTION

Figure 1:
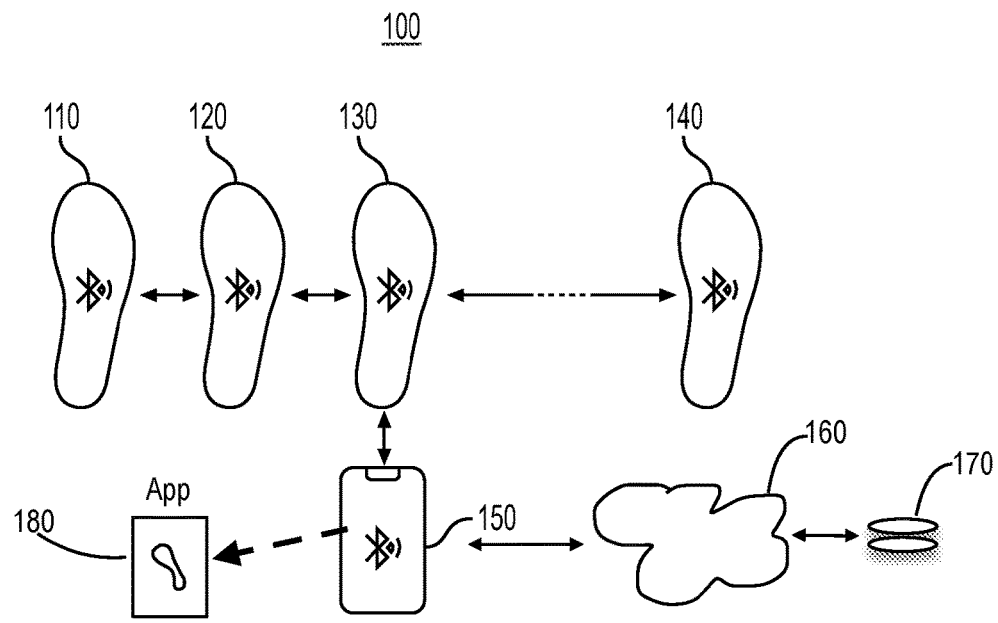
FIG. 1 is a flow diagram illustrating wireless communication between exemplary devices with a portable smart device.

In one or more embodiments, the exemplary "wearable" device is body-part conforming and non-intrusive, being comprised of a shoe insole, sock, shoe, or foot attachment (heretofore referred to as "insole") for balance training. In other embodiments, the exemplary device can take the form of an ankle, knee, elbow, etc. wearable sleeve. The wearable device is embedded, in a non-intrusive manner, with a powering device (e.g., battery), a microcontroller, a wireless communication module, one or more bio-mechanical measuring sensors and at least one feedback module that provides one or more haptic, vibrational, audio, visual, kinesthetic, tactile, olfactory, thermal, vestibular or somatosensory feedback.

The exemplary embodiments are designed to have a form factor that unites all the sensors, feedback mechanisms and electronics into a single wearable "housing" that is non-intrusive to the user, and wirelessly communicates with a smart device in close proximity.

In some embodiments, the bio-mechanical measuring sensor can simply be a pressure sensing unit. This pressure measurement unit can be comprised of a layer of a pressure-sensitive material placed between two or more layers of a grid of conductive material, which are electrically connected to the printed circuit board. In various embodiments, an inertial measurement unit (IMU) is embedded, operating as one or more of a gyroscope, an accelerometer or a magnetometer, within the sleeve or insole. In some embodiments, additional measuring and/or feedback units are placed on other body parts to provide a synergistic system between the body parts.

In various embodiments, sensor systems are described that may collect data related to pressure in one or more locations, movement, temperature, velocity, acceleration, and/or biometric information, which includes but is not limited to weight, heart rate, blood pressure or cholesterol levels. These data can be used for analysis purposes and for real-time feedback to the user of the sensor system.

The exemplary embodiments described herein enable data to be compared and correlated to other performance data, such as the outcome of a golf shot or baseball pitch in order to discover the best physical practices for achieving the desired outcome under various conditions. The best practice may be different for individuals of different gender, height, weight, age, or other such variables, or dependent on the sport, activity, or task.

For example, the bio-mechanics of an expert golfer can be determined to provide a subsequent user real-time feedback, enabling the user to imitate the expert, to understand deviations from the expert, and to match the user with the most appropriate expert to imitate. The exemplary system allows for imitation with real-time correction or repetition with feedback phases of mastering a skill.

In some embodiments, AI is used to analyze measured data to determine successful patterns and to match trainees with the most effective training feedback system. Machine learning or other forms of artificial intelligence (AI) may be used to analyze such physical data for various purposes. For example, AI could be used to determine which physical measures, the sequence of measures, or synchronous combination of measures most likely lead to the desired outcome. In other examples, AI could be used to collect data from an expert golfer and use it to train a novice golfer to improve his/her swing or foot balance. In another example, AI could be used to determine which subset of measures obtained in experts best match a particular user or trainee: AI may determine that a trainee that is an elderly patient with Parkinson's disease learns best when training to emulate another Parkinson's patient with less advanced gait disturbance. Alternatively, the matching system could determine which specific measures of pressure or motion in which specific locations are most predictive of a positive outcome. In another example, AI may determine the best cross-training models, so that a golfer improves most by first learning to emulate the foot weight transfer of a slalom skier. Or the system may determine that a right-handed golfer performs best when initiating the front swing by synchronously initiating pressure on the medial side of the right foot while starting forward motion of the left wrist, all while keeping the head from moving leftward. In another example, AI may be used to train a marching band to perform in synchronous or asynchronous behavior. Alternatively, the AI system could learn events that are sequential and synchronous and learn the timing between events.

In addition, the AI system could learn and/or a Balance Learning System (BLS)—having the device(s) and mechanisms described herein—could enable a user to manually set a specific task to be trained or monitored among a larger set of tasks associated with a sport or activity. For example, when a golfer is putting, pitching, and taking a full swing, desired pressure and motion measures may be quite different. For example, when putting, the goal may be no foot pressure changes or head movements, whereas, during a full swing, the goal may be a shift of weight to the back foot with a slight posterior lateral head movement followed by a shift of weight to the front foot with limited head lateral movement. The precise desired measures may, therefore, vary depending on the specific task, whether related to a sport or other activity, so it is useful for the system to either automatically anticipate the specific task or allow the user to specify the task.

FIG. 1 is a flow diagram 100 illustrating a wireless communication "web" between exemplary wearable "bio-sensor" devices 110-140 (configured here as one or more sole/foot sensing device(s)) with use of a portable smart device 150. While only one portable smart device 150 is shown, it is understood that additional smart devices may be used. A Bluetooth® (owned by the Bluetooth SIG) symbol is shown as the mode of communication between the exemplary wearable device(s) and the smart device(s) 150, but it is expressly understood that other wireless communication protocols/approaches may be used, depending on implementation preference and design. Control and/management of one or more of the various wearable device(s) can be achieved through a bio-sensing and/or feedback "app" 180 or software running on the smart device(s) 150. In some embodiments, with multiple smart devices and wearable devices, information may be communicated between "different" smart devices and "different" wearable devices, allowing for cross communication. While the smart device 150 is shown here as having the form of a smart phone, other communication and user interface devices may be used, non-limiting examples being a smart watch, smart glasses, tablet computer, smart earphones, etc.

The smart device may also be in communication through a cloud-based network 160 to a server 170 having additional features, software, processing capabilities. Here, it is envisioned the server 170 can provide data analysis as well as data storage and for controlling the smart device(s) 150's app 180, as appropriate. The aspects of software communication and software client-server, app arrangements and control are well known in the arts, and are incorporated herein as being under the purview of one of ordinary sill. For example, AI may be implemented on the server 170 and the information forwarded to the smart device's app 180, or even to one or more of the wearable device(s) 110-140.

As one possible example of use, a first wearable device 110 may be worn by an amateur while second wearable device 120 may be worn by a professional. And movements of the professional can be signaled to the amateur's device (110) via feedback so as to train the amateur to "match" the foot position/balance of the professional's.

Figure 2:
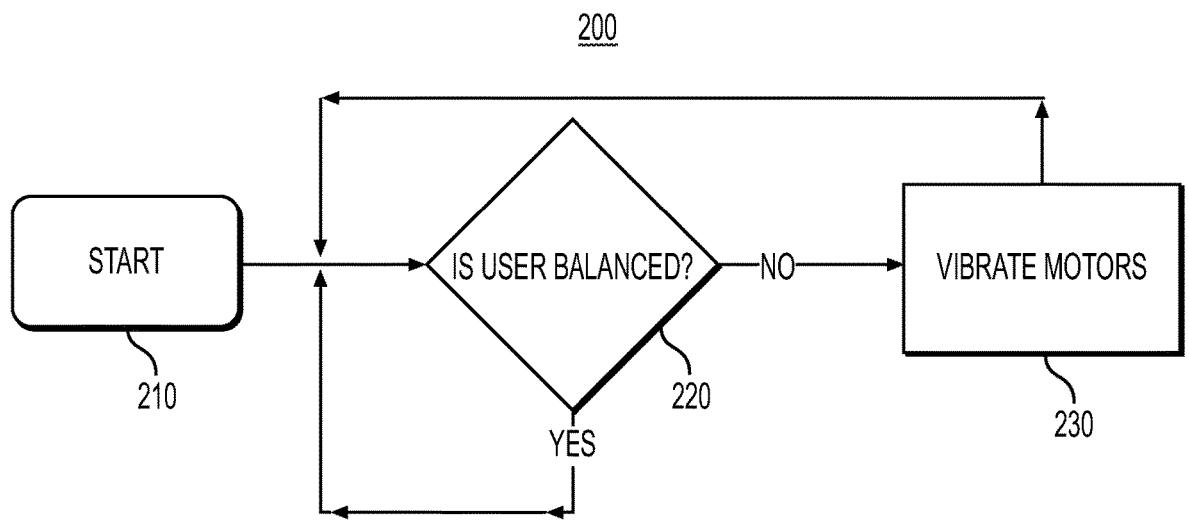
FIG. 2 is a block diagram showing a feedback loops that check for user stability and act accordingly.

FIG. 2 is a block diagram showing an exemplary repeating process 200 for one or more exemplary "bio-sensor" wearable devices. The repeating process 200 provides feedback loops that check for user conformance and act accordingly. After the exemplary wearable device (for example, one or more of embodiments 110-140 of FIG. 1) starts 210, the process 200 checks 220 whether starting measurement(s) obtained from the exemplary wearable device match a predetermined starting threshold, range, or value. In this example, it can be considered a "starting balance" when using an insole like wearable device. If the user is not in the proper starting balance, the exemplary wearable device activates a cueing mechanism to provide feedback to the user, shown here as step 230 to vibrate insole motors—sending a tactile response to the user's foot. The exemplary process 200 thereafter repeats step 220 for the next measurement cycle. If the starting measurement(s) match the "starting balance," the exemplary process 200 returns to step 220 for the next measurement cycle. Termination of the process 200 can via user selection at any point in the process. It is understood that this example is for an insole like wearable device, therefore for a non-sole like device, step 230 (providing feedback) may be through an alternative mechanism, for example, a sound, combination of sounds, vibration, change in temperature, constriction, color change, etc., according to the device's configuration.

Figure 3:
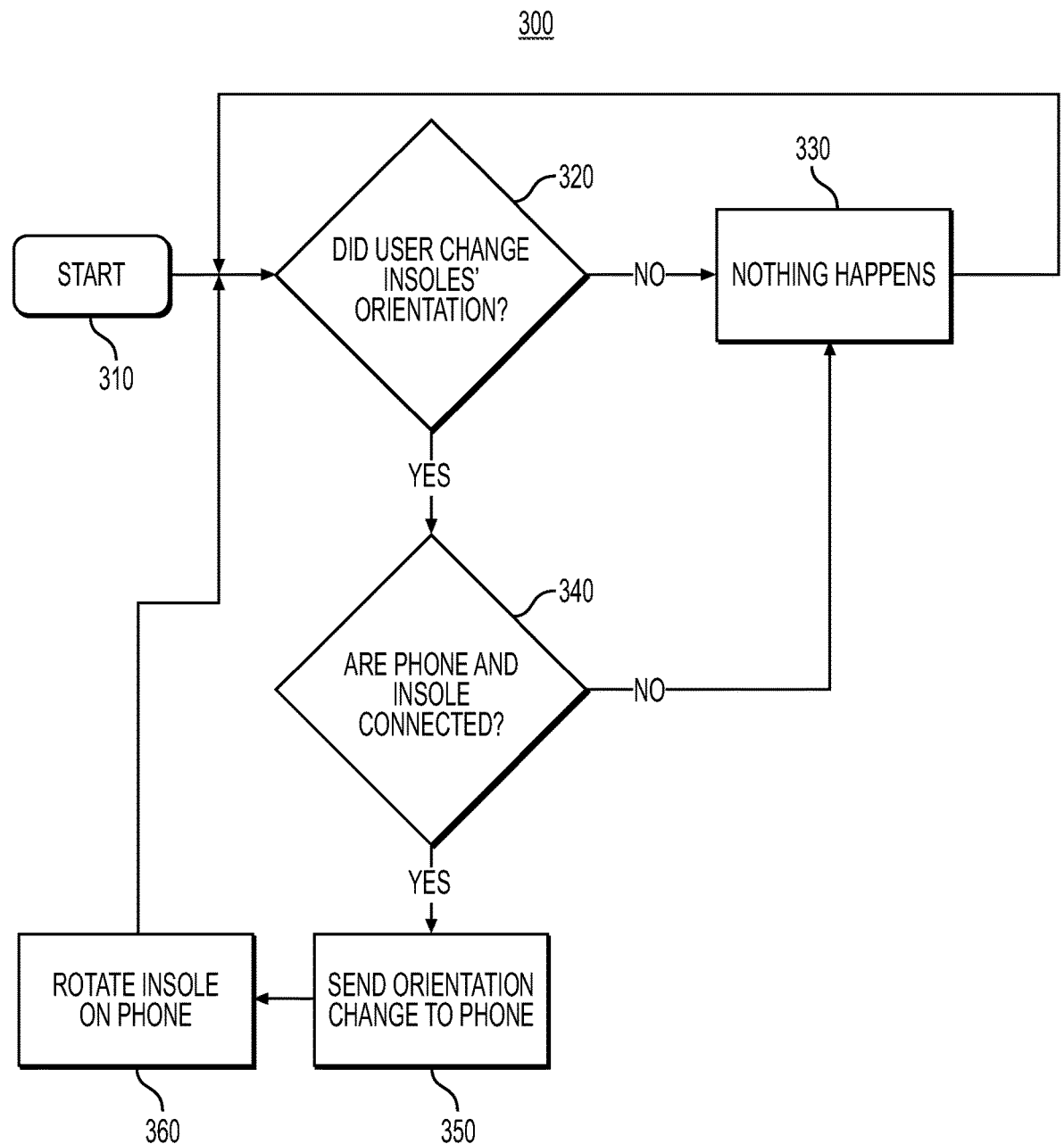
FIG. 3 is an exemplary flowchart illustrating various loop(s) that carry out real-time foot orientation visualization on a mobile application on a user's smart device.

FIG. 3 is an exemplary flowchart 300 illustrating various loop(s) that carry out real-time foot orientation visualization on a mobile application on a user's smart device, for a wearable insole like device (for example, one or more embodiment(s) 110-140 of FIG. 1). Upon start 310 of the exemplary wearable device, a test 320 is performed to see if the user has changed his insoles' orientation from any one or more of a default position, from a prior stored position, or other characteristic. If the answer is no, the process 300 does not act and returns to step 320 for the next test cycle. If the answer is yes, the process 300 proceeds to step 340 to determine if the wearable device is "connected" to the user's smart device, or vice versus. If the answer is no, then the process 300 does not act and returns to step 320 for the next test cycle. If the answers to both steps 320 and 340 are yes, then the process 300 proceeds to step 350 where a change of visualization via step 360 is performed on the mobile application. The mobile application then pictures the virtual insole accordingly. It is presumed here that the mobile application has an illustration of the insole's orientation displayed on its interface, and changes therefore are transmitted to the display. In some embodiments, the orientation may be the only form of visualization. In other embodiments, different pressures, temperatures and other forms of biomechanical information may be displayed, according to design preference.

Sensors in the exemplary systems can be linked between two or more individuals (for example, dancers) to collect data and/or provide real-time feedback to assist the two or more individuals in coordinating their desired motions, pressures, and timings.

Figure 4:
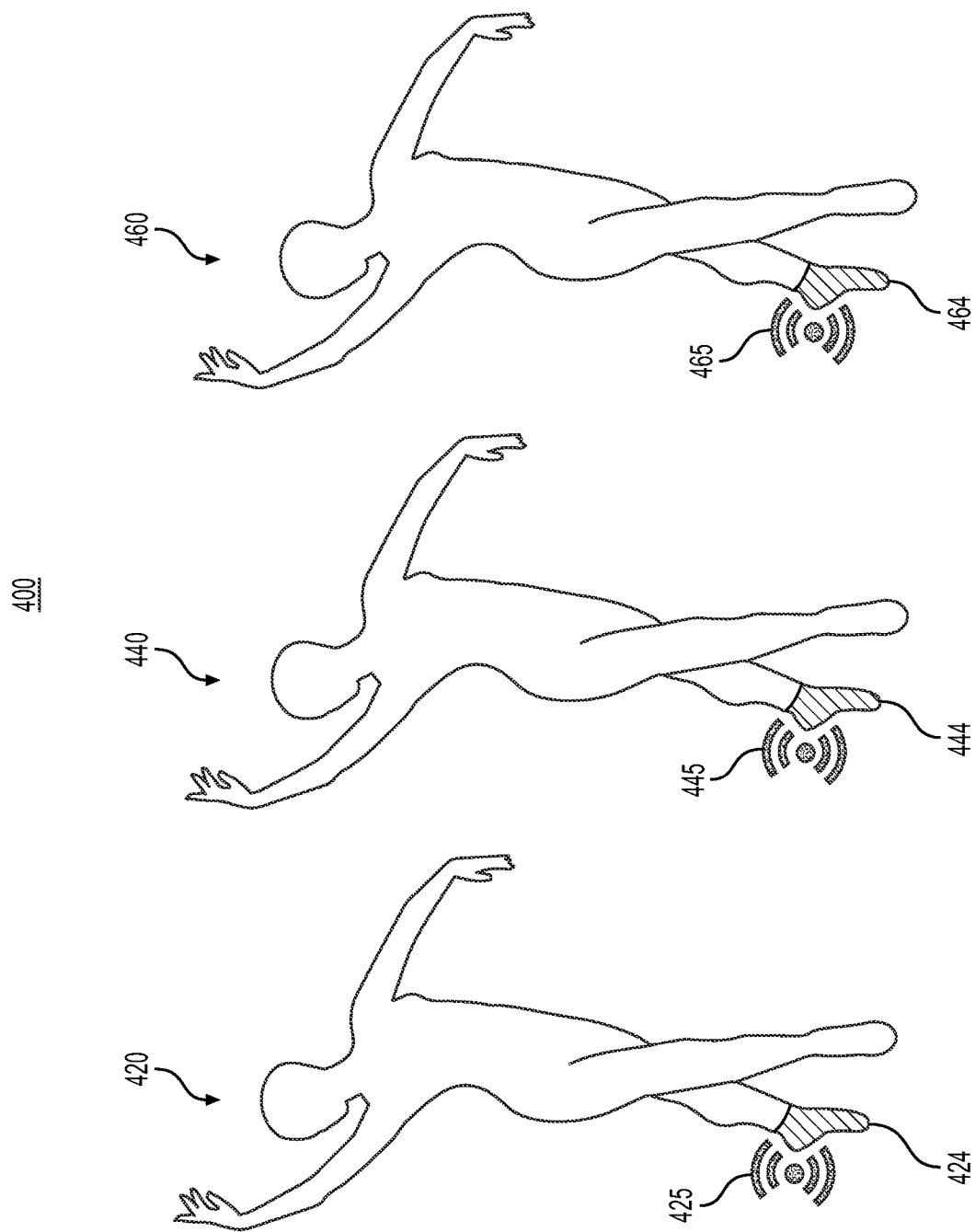
FIG. 4 depicts an example of coordinated usage of the balance system, wherein several dancers can coordinate their movements based on cues from the system.

FIG. 4 depicts an example of coordinated usage of the exemplary system, wherein several 420, 440, 460 dancers can coordinate their movements based on cues from an insole-like wearable system. Here, the device 424, 444, 464 can be inside or part of a sock or stocking, or shoe that sends wireless signals 425, 445, 465 to the respective dancers' smart devices (not shown). Or to each other. That is, while the previous examples detail feedback from a wearable device to its user's foot (or body part) and/or to the user's smart device, it is contemplated that one wearable device may send a wireless signal to a neighboring $2^{nd}$ wearable device (directly or indirectly) so as to cue that $2^{nd}$ user to move upon the trigger. As a non-limiting example, 1st dancer 420 may lift her foot, which sensed by the $1^{st}$ dancer's wearable system 424, which can trigger a wireless signal to $2^{nd}$ dancer's device (or wearable sensor 444) to vibrate, etc. the $2^{nd}$ dancer's foot. $2^{nd}$ dancer can then respond to the signal and move her foot. By recognizing different triggering signals, the dancers may coordinate movement solely via the wearable sensors' interaction with each other. Typically, coordination between dancers is based on timing or music signals. Sight or sound impaired dancers may appreciate the benefits afforded by this system. As can be imagined, sensor feedback may be of a single type or multiple "types" and arrangements.

It should be apparent, one or more additional pressure, velocity, or motion sensing devices can be attached to one or more body parts so that measures of these body parts can be made, and the sequences of measures can be assessed. For example, in a golfer, the system may measure the sequence of foot pressure changes and upper body or pelvis motions.

Figure 5:
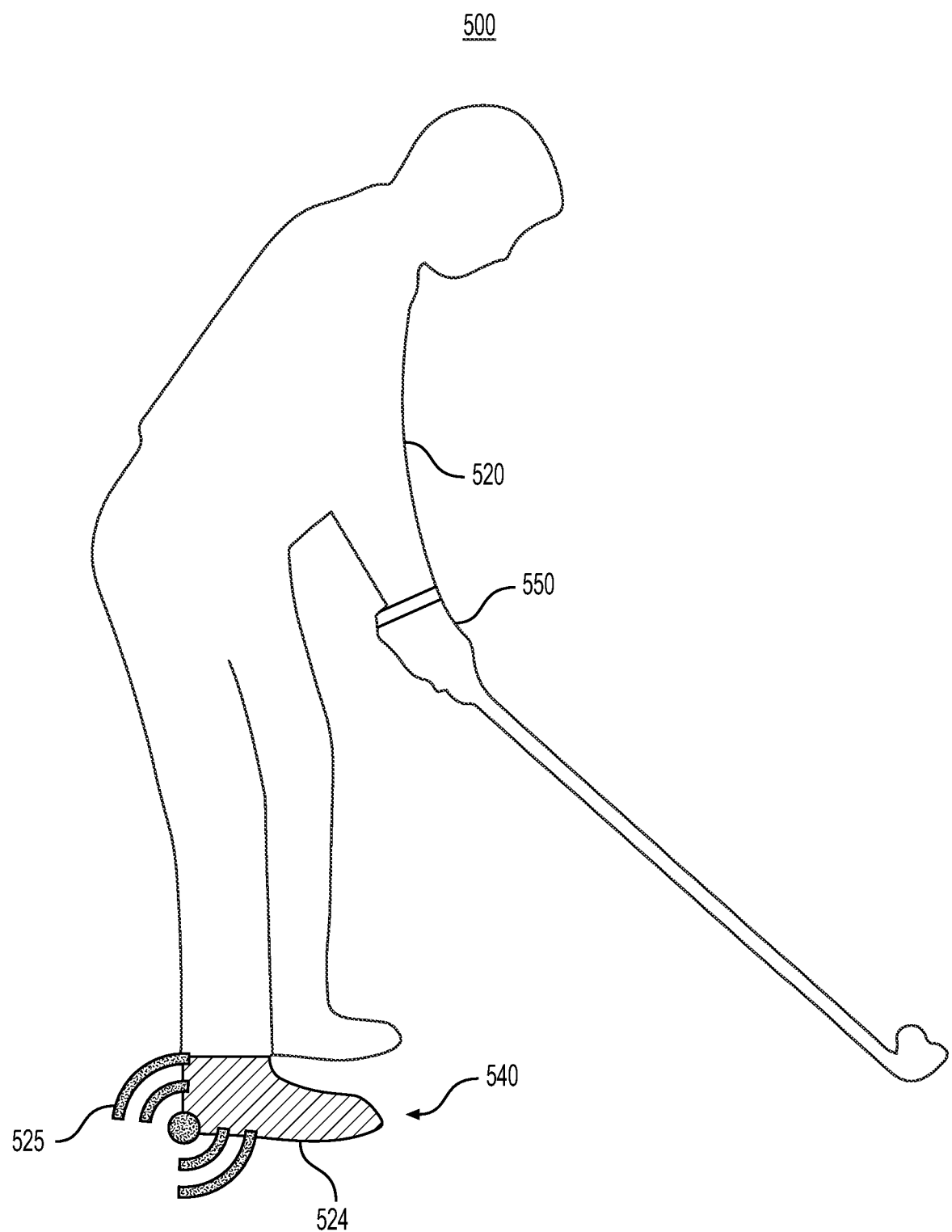
FIG. 5 depicts an example application of the balance system, wherein a golf player uses the system to receive cues to change their stance for better balance.

FIG. 5 depicts an example application 500 of an exemplary system, wherein a golf player 520 uses an exemplary system to receive cues to change his stance for better balance, as dictated by software running on his smart device (not shown). Here, only one exemplary system's wearable sensor 524 and wireless communication 525 is shown on one of the golfer's foot 540. However, both feet may have a coordinated system. Further, exemplary wearable bio-sensored gloves may be configured having similar capabilities.

The exemplary system can contain (via a smart device in communication to the wearable sensor 524) a graphical user interface or other programmable interface enables the system to detect when the proper starting position has been achieved and/or when the specific task has been initiated and/or completed. Thus, for example, in one embodiment, the system may be programmed (using machine learning, for example) to automatically recognize, based on a golfer's foot position and motion, that he or she is about to initiate a putting stroke, and can similarly determine when the stroke is complete. In one embodiment, the user receives real-time feedback to help achieve the desired or optimal starting stance, and he receives a real-time signal to begin the stroke or other action. In another embodiment, after the user achieves the desired stance, the system begins to automatically initiate measurements of the stroke. In another embodiment, the system measures the time between achieving the stance and initiating the stroke, or the timing of the back-swing relative to the front-swing. While these examples relate to the game of golf, the same principles may apply to a wide range of balance-related activities.

Figure 6:
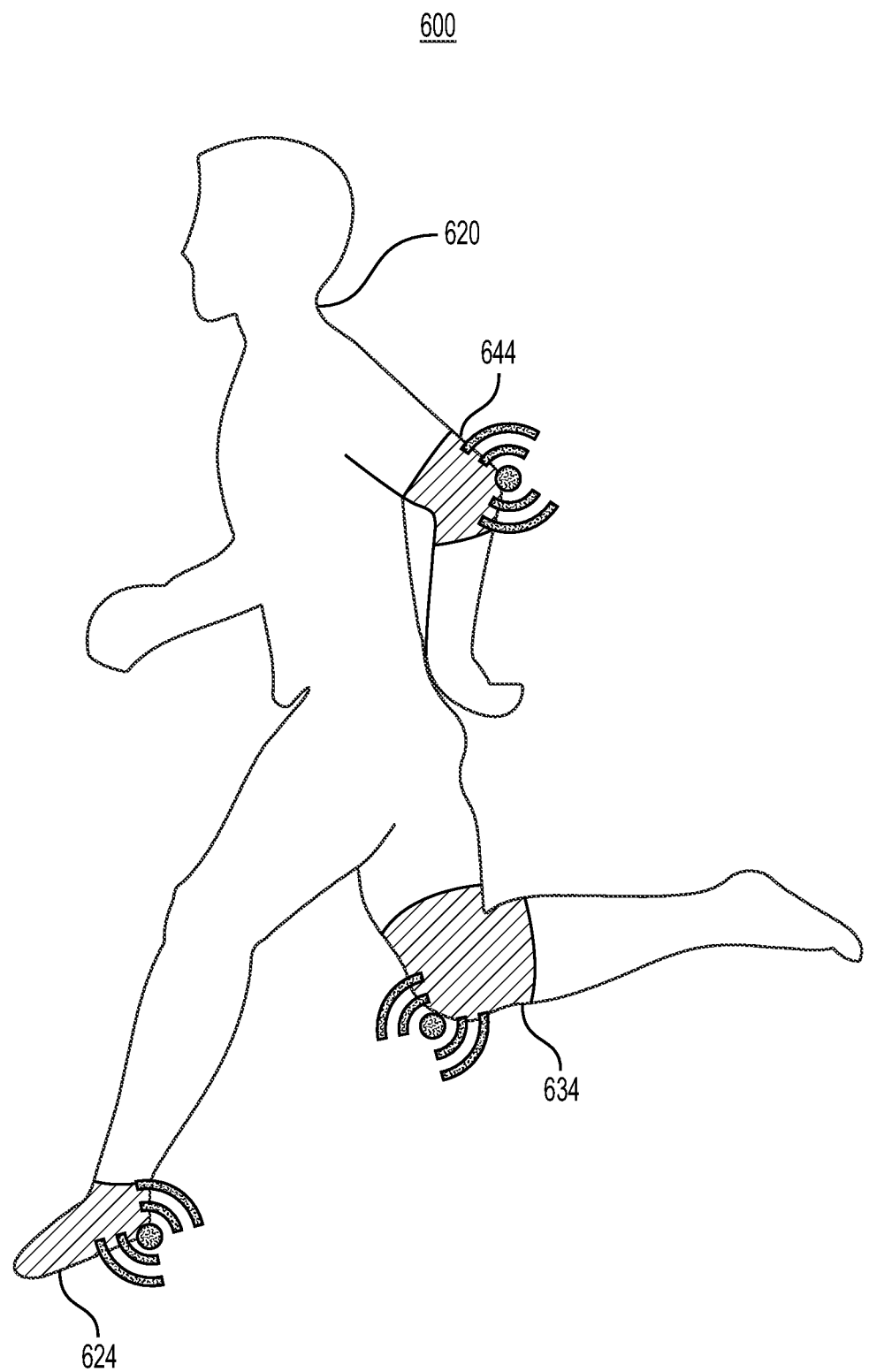
FIG. 6 depicts an example of usage of the system where it communicates with other sensors and related electrical devices on the body to provide holistic analysis and feedback to an athlete.

FIG. 6 depicts an example of usage of an exemplary system having different body part wearable configurations. Runner 620 may have a foot wearable wireless bio-sensor device 624, a knee wearable wireless bio-sensor device 634 as well as an elbow wearable wireless bio-sensor device 644. The bio-sensor device(s) and accompanying hardware (not shown) are embedded into recesses in a wearable housing (illustrated here as a sleeve) which is flexible, and body-part conforming. The exemplary system can communicate jointly to a smart device (not shown) worn by the runner and/or between each other (for example, from the knee bio-sensor device 634 to the foot bio-sensor device 624, the latter having a master controller, if so desired). Having measurement and feedback capabilities on the primary joints for a runner can provide invaluable real-time 'training" feedback. For example, if the runner's knee is not sufficiently bent high enough for best running practices according to a predetermined parameter, the exemplary knee wearable wireless bio-sensor device 634 may vibrate or send some other feedback signal to the runner to indicate the need to bend higher. The feedback can also be signaled to the runner's smart device, for example, as a changing image, color, tone or vibrations, or other metric, allowing the runner to continue performing without having to interrupt his training to evaluate his performance. Therefore, real time adjustments can occur during actual running to provide instant or near real time evaluation and improvement. This approach is in complete contrast to conventional methods where training is based on non-feedback sensors that simply measure the parameters which are evaluated against desired parameters after the training session is over.

It is understood that the various wearable bio-sensor devices 624, 634, 644 may communicate or send signals to each other, either directly (through near field wireless) or indirectly (hopping from the runner's smart device to the next wearable sensor). In this scenario, one wearable bio-sensor device may detect a certain condition and relay that information for action by another wearable bio-sensor device. For example, an "elbow" bio-sensor device may constrict, vibrate, tone, etc. in response to the knee bio-sensor device's triggering.

Figure 7:
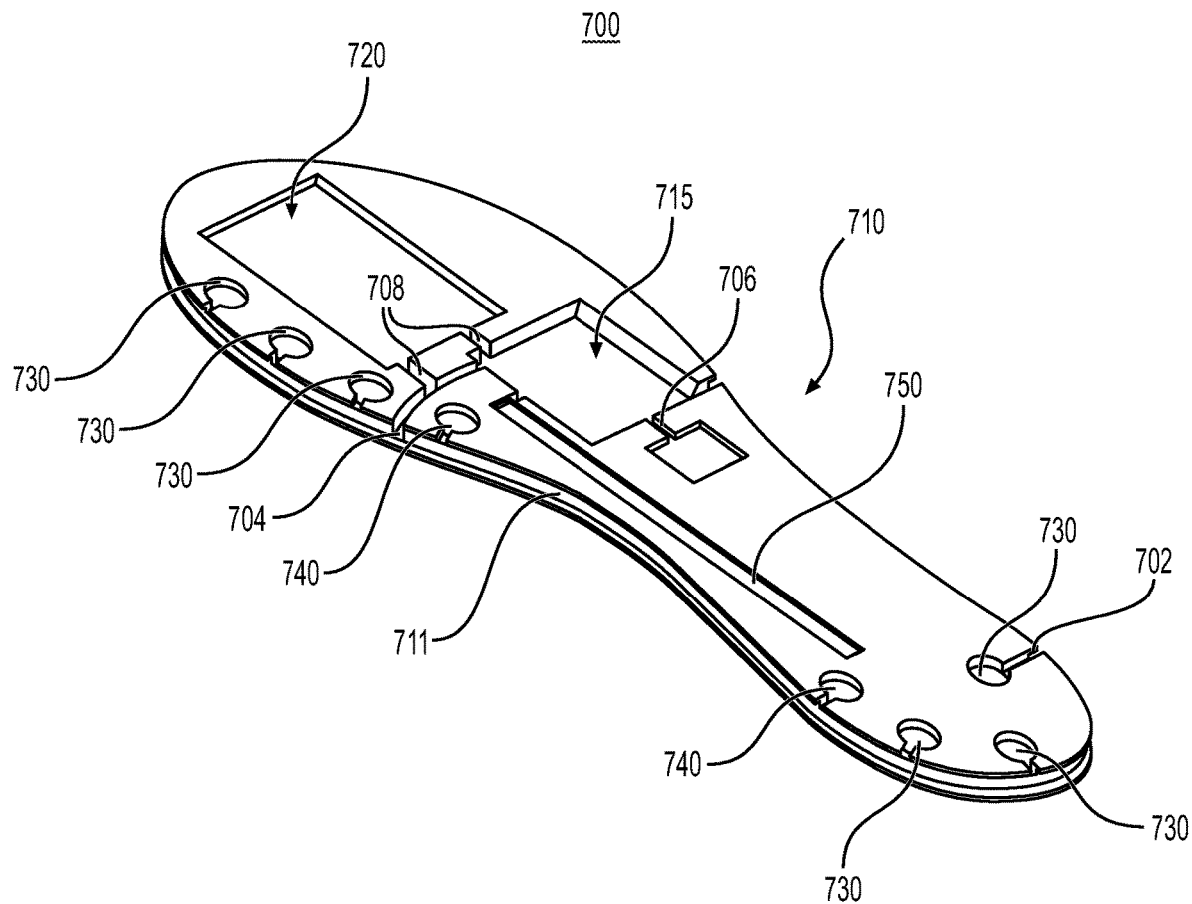
FIG. 7 depicts an exemplary embodiment of an insole like bio-sensor device.

FIG. 7 depicts an exemplary embodiment 700 of an insole like bio-sensor wearable device 710. Channels 702, 704, 706, 708, 711 depict various wire channels with wires that are routed across the insole 710 connecting various components of the exemplary device 710 housed in recesses or cavities in the insole 710. Other wire channels, wires and locations are possible. 712 signifies an electronic assembly for a printed circuit board (PCB) having a "controller" as well as associated communication circuitry (including a wireless transmitter/receiver). 720 signifies a power supply which may be a battery (long lasting or rechargeable). Sensors 730 are distributed around specific locations on the device 710. In this example, the primary sensors 730 are located near the periphery, with one or more optional feedback mechanisms 740 in proximity. It is expressly understood that the arrangement, number of, shape, etc. of sensors 730 and feedback mechanisms 740 may vary, depending on design parameters, type of use, etc. As a non-limiting example, a sports-related system may have more sensors/feedback units imbedded in the insole embodiment vs. a system used by elderly solely for walking balance.

It is expressly understood that the various electronics in the above and below embodiments may be directly or indirectly connected to each other. As a non-limiting example, sensors 730 may be indirectly connected to electronic assembly 712 via wires through/into feedback mechanisms 740. Other non-direct routes to the PCB may be possible, according to design preference.

The particular arrangement shown in FIG. 7 envisions a sports type configuration where the sensors 730 are placed along a curving run inside edge of the foot near the ball of the big toe and a semi-circle around the heel. As seen in FIG. 7, some of the sensors 730 may be further inwards than other sensors. While the sensors 730 are shown as being circular they may be of a different shape, based on the sensor type and sensing physics. As should be apparent, the placement of the sensors at specific locations on the insole 910 can provide different "balance" measurements which are used to determine appropriate foot positioning and weight distribution.

A pressure measurement unit 750 is shown here as spanning a region of the arch of the foot but can be located at other portions of the insole, according to design preference. The pressure measure unit 750 can be formed from a pressure-sensitive material, for example, a pressure resistive material, placed between two or more layers comprising of a grid or strip of conductive material, which is electrically connected to the PCB 712. The strips on any one of these layers can be orthogonal to the strips on the other layer. Of course, other types of pressure detecting materials and approaches may be used.

As discussed above, the sensors 730 can be of the form of inertial measurement units embedded within the cavities or recesses formed in the base of the insole. In various embodiments, the inertial measurement unit can be a gyroscopic device and a linear acceleration measurement device. In other embodiments, the inertial measurement unit may be of any electrical or magnetic device capable of measuring the force, orientation, and/or angular rate of the insole.

In a prototype embodiment, the sensors 730 were approximately 10 mm in diameter, and 2.7 mm in height. The feedback mechanism 740 were of similar dimensions and the feedback was via micro vibration motor(s).

Figure 8:
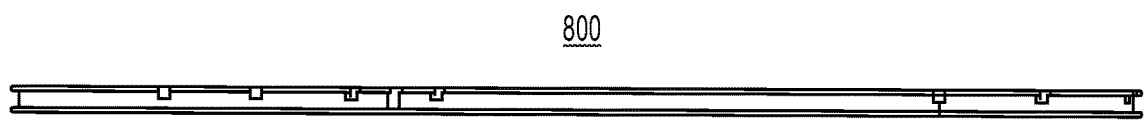
FIG. 8 is a side profile illustration of the exemplary insole device of FIG. 7.

FIG. 8 is a side profile illustration 800 of the exemplary insole device of FIG. 7. A PCB and other electronics are embedded into voids in the base of the insole so that it does not protrude into the user's sole. In various embodiments, the PCB is comprised of an embedded microcontroller chip and related electrical components, such as a wireless communication module. The wireless communication module is capable of wirelessly transmitting balance data collected and packaged by the microcontroller. This data can be transmitted to either a handheld mobile device or another insole equipped with a similar or dissimilar wireless communication module.

As alluded in FIG. 7, these components are electrically connected (through various wire channels). In other embodiments, the PCB may also include any number of multiplexer chips to aid the functionality of the microcontroller, communications, etc.

Figure 9:
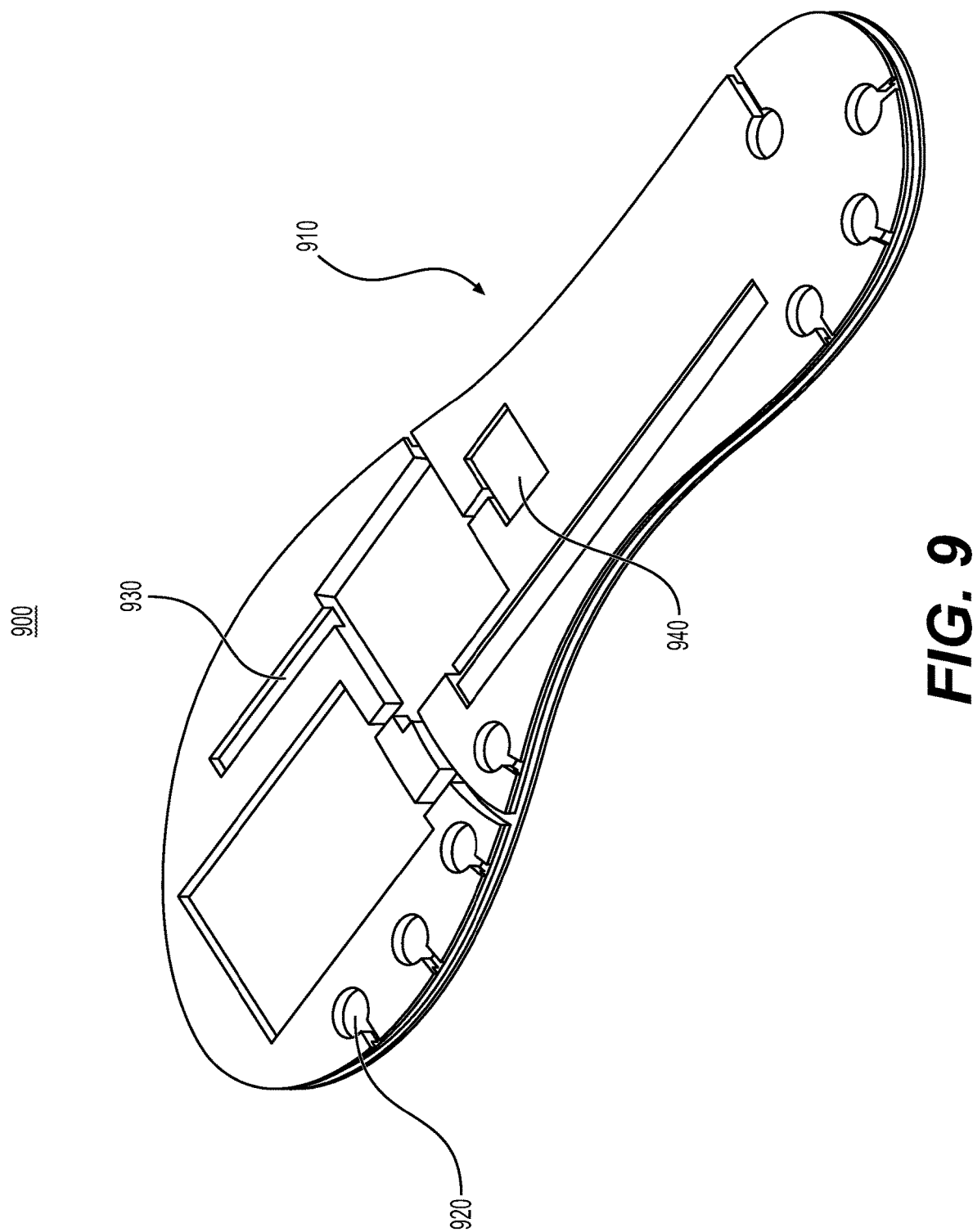
FIG. 9 is an illustration of a variation of the embodiment of FIG. 7.

FIG. 9 is an illustration 900 of a variation of the embodiment of FIG. 7. 920 indicates one possible placement of a cueing/feedback mechanism. 930 indicates one possible placement of another pressure measurement unit for measuring flex at the instep. 940 indicates one possible placement of the initial measurement unit (IMU). The inertial measurement unit (940) can be a gyroscope, an accelerometer or a magnetometer, etc. or a combination thereof, embedded within the insole 910. Typically, but not necessarily, the IMU can be a circuit board containing the one or more measurement sensors. It is understood that all of the mechanisms above are "embedded" into accommodating cavities or recesses in the insole 910 so as to not protrude into the user's foot to cause discomfort.

Figure 10:
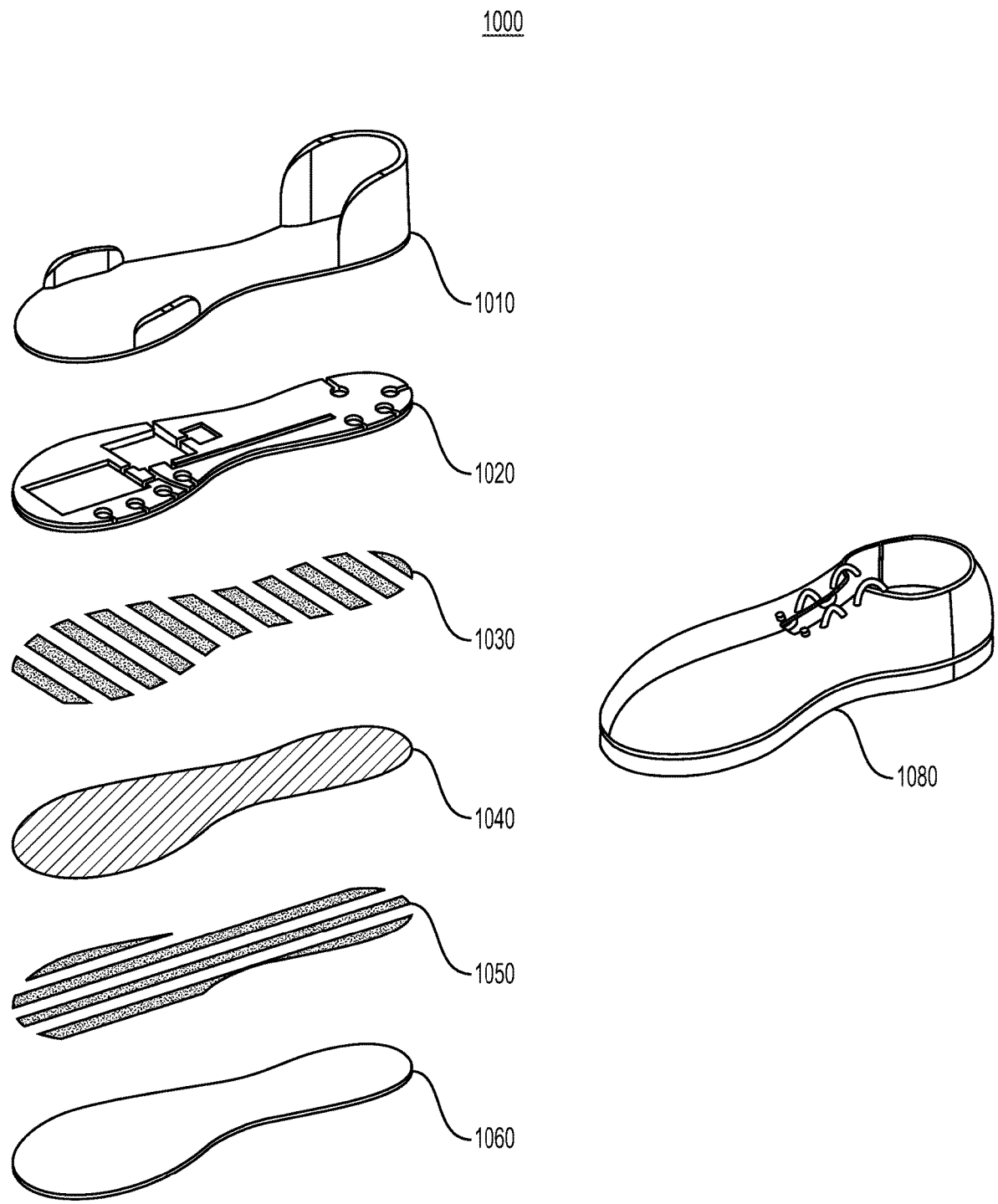
FIG. 10 is a blow-up illustration of another exemplary insole embodiment.

FIG. 10 is a blow-up illustration 1000 of another exemplary insole embodiment. Top cushion layer 1010 sits over sensor insole layer 1020. Below sensor insole layer 1020 is a full insole pressure sensor composed of top strips 1030, intermediate pressure resistive substrate 1040 and orthogonally oriented bottom strips 1050, connected electrically to the sensor insole layer 1020. A bottom cushion layer 1060 isolates the above elements from the sole of the shoe 1080. Obscured from view are electrical contact(s) between the sensor insole layer 1020 and the below full insole pressure sensor.

Since the exemplary system and devices are electronic in nature, an optional graphical user interface or other programmable interface can provide the user the ability to specify the specific upcoming task, such as putting vs. a full swing, etc. so that measurements can be classified by specific tasks and feedback provided per specific task. In addition, data can be thus aggregated by a specific task.

Data from the wearable sensors can be collected, and management reports are generated compiling and/or summarizing such items as the frequency of training, duration of the training, time of data of training, day of the week of training. Such data and summaries can be reviewed by the user or by others depending on programmable user preferences, user roles, and user rights. In one embodiment, for example, a user can review the data related to each putt taken during a round of golf and compare to other rounds of golf played over a span of time. In one embodiment, a coach or teacher with many students can review the data from multiple students that are practicing at the same time or asynchronously. In one embodiment the system presents a score that reflects how successful the user is in achieving the desired performance measurements to show progress or lack of progress. In one embodiment, users can see other user's scores to facilitate competition. These embodiments may facilitate user engagement and therefore more successful achievement.

The collected data for a user and/or group of users can be employed to track the progression of a degenerative disease, the benefits of training, or the benefits of medical or physical therapy. Therefore, an additional aspect described herein is the use of the BLS to objectively measure a disease, such as a Parkinson's related gait disorder to facilitate pharmaceutical assessment in a clinical trial or another clinical environment. The invention may also enable objective assessment of non-pharmacological modes of therapy. In one embodiment, the BLS can be used to objectively measure the risk of an accidental fall, which may help healthcare organizations and others classify patients as to the level of required supervision. In another embodiment, the BLS can be used to track actual falls to help in risk assessment or assess to effectiveness of an assistive device, such as a walker. In another embodiment, the system can be used to track gait or other physical performance to determine the level of a person's alertness, consciousness, or impairment. For example, certain medications or drugs such as alcohol may result in gait disturbance. The BLS may provide an objective measure of the effects of such medication or drugs, perhaps even providing an objective measure of sobriety. Some diseases result in patients developing a wide-based gait. The BLS may provide an objective measure of such manifestations, progression, or regression of such diseases.

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

What is claimed is:

1. A wearable, feedback providing bio-sensing system, comprising:
   a bio-sensing and feedback program running on a user's smart device, the program receiving wireless data transmitted from a proximal wearable bio-sensing device, the wearable bio-sensing device comprising:
      a bio-sensor housing shaped as an insole, planar and flexible with one or more first recesses containing
      a controller,
      a powering source,
      a wireless communication module;
      one or more feedback mechanisms providing at least one of a haptic, vibrational, audio, visual, kinesthetic, tactile, olfactory, thermal, vestibular, and somatosensory feedback to a wearer of the bio-sensor housing, at least one of the feedback mechanisms embedded in one or more second recesses in the bio-sensor housing, the feedback being triggered by the controller from instructions sent by the bio-sensing and feedback program;
      a three-layered pressure sensor shaped as an insole matching the insole shape of the bio-sensor housing, communicating a measurement to the controller and disposed under the bio-sensor housing, comprising:
         a first top layer of parallel strips of conductive material extending approximately to a perimeter of the pressure sensor's insole shape;
         a second solid layer of a resistive material extending approximately to the perimeter of the pressure sensor's insole shape; and
         a third bottom layer of parallel strips of conductive material oriented orthogonally from the first layer of conductive material and extending approximately to the perimeter of the pressure sensor's insole shape,
   wherein the triggered feedback indicates to the user that the measured at least one pressure, movement, temperature, velocity, and acceleration conforms or does not conform to a desired parameter, enabling the user to perform real-time adjustment of his activity.

2. The bio-sensing system of claim 1, wherein at least one of the one or more first and second recesses form a single larger recess.

3. The bio-sensing system of claim 1, further comprising a server, the server communicating with the smart device, and performing an analysis of data from the smart device's received sensor measurements.

4. The bio-sensing system of claim 3, wherein the bio-sensing and feedback program are separate programs.

5. The bio-sensing system of claim 3, further comprising an artificial intelligence program running on the server and analyzing the data from the smart device's received sensor measurements.

6. The bio-sensing system of claim 1, wherein the one or more sensors are disposed proximal to a ball-of-foot location on the insole and a heel location on the insole.

7. The bio-sensing system of claim 1, wherein the transmitted wireless data is communicated via Bluetooth® between the user's smart device and the wearable bio-sensing device.

8. The bio-sensing system of claim 1, wherein the smart device is a smart phone, smart watch, smart glasses, tablet computer, or smart earphones.

9. A method to provide real-time feedback to a user's physical activity, comprising:
   running a bio-sensing and feedback program on a user's smart device;
   receiving wireless sensor data transmitted from a user-worn, flexible bio-sensing and feedback device having an insole shaped planar housing with a recess to contain sensing electronics to sense at least one of foot pressure, movement, temperature, velocity, and acceleration, feedback electronics to send physical feedback to the user, the bio-sensing and feedback device further having a three layered pressure sensor with a matching insole shape to and under the planar housing, the pressure sensor comprised of a full insole shaped resistive substrate with a first plurality of conductive strips distributed in a first direction along a length of a top of the resistive substrate and a second plurality of conductive strips distributed in a second substantially orthogonal direction from the first direction along a length of a bottom of the resistive substrate;
   monitoring the user's activity through the sensing electronics;
   comparing the at least one of pressure, movement, temperature, velocity, and acceleration of the physical activity to a desired parameter via the bio-sensing and feedback program; and
   sending real-time at least one of a haptic, vibrational, audio, visual, kinesthetic, tactile, olfactory, thermal, vestibular, and somatosensory feedback to the user, to indicate the user's physical activity conforms or does not conform to the desired parameter, enabling the user to perform real-time adjustment of his activity.

10. The method of claim 9, further comprising:
    sending the receiving wireless sensor data to a server connected to the user's smart device;
    processing the sensor data; and
    sending instructions to the user's smart device to trigger a feedback in the user-worn, flexible bio-sensing and feedback device.

11. The method of claim 9, further comprising performing artificial intelligence on the sensor data.

12. The method of claim 9, wherein the user wears the flexible bio-sensing and feedback device as a shoe insole or a sock.

13. The method of claim 9, wherein the method provides a real-time balance learning methodology.

14. The method of claim 9, wherein at least one of weight, heart rate, blood pressure and cholesterol level biometric information on the user is obtained.

15. The method of claim 9, wherein the method is used to improve the user's performance with a sport.

16. The method of claim 9, wherein the method is used to track the user's progress with a medical or physical condition.

* * * * *